(12) United States Patent
Shimodaira et al.

(10) Patent No.: US 6,444,167 B1
(45) Date of Patent: Sep. 3, 2002

(54) METHOD OF FORMING UNDERCUT IN METAL POWDER INJECTION-MOLDED ARTICLE

(75) Inventors: Kenichi Shimodaira, Komagane; Junichi Hayashi, Okaya; Masaru Kato, Chino, all of (JP)

(73) Assignee: Injex Corporation (JP)

( * ) Notice: Subject to any disclaimer, the term of this patent is extended or adjusted under 35 U.S.C. 154(b) by 0 days.

(21) Appl. No.: 09/554,710

(22) PCT Filed: Sep. 13, 1999

(86) PCT No.: PCT/JP99/04998
§ 371 (c)(1),
(2), (4) Date: May 17, 2000

(87) PCT Pub. No.: WO00/16935
PCT Pub. Date: Mar. 30, 2000

(30) Foreign Application Priority Data

Sep. 18, 1998 (JP) .................................. 10-264987

(51) Int. Cl.⁷ ................................................. B22F 1/00
(52) U.S. Cl. ............................................ 419/37; 419/38
(58) Field of Search ............................. 419/36, 37, 38

(56) References Cited

U.S. PATENT DOCUMENTS

| | | | | |
|---|---|---|---|---|
| 5,267,854 A | | 12/1993 | Schmitt ........................... 433/8 |
| 5,393,486 A | * | 2/1995 | Eckert et al. .................. 419/66 |
| 5,641,920 A | * | 6/1997 | Hens et al. .................... 75/228 |
| 5,773,099 A | * | 6/1998 | Tanaka et al. ............... 427/529 |
| 5,972,269 A | * | 10/1999 | Barros et al. ................. 264/221 |

FOREIGN PATENT DOCUMENTS

| | | |
|---|---|---|
| EP | 0 682 999 A2 | 4/1995 |
| EP | 0 707 833 A1 | 10/1995 |
| JP | 62-199701 | 9/1987 |
| JP | 3-53002 | 3/1991 |
| JP | 3-120996 | 12/1991 |
| JP | 3-277814 | 12/1991 |
| JP | 5-171334 | 7/1993 |
| JP | 6-212206 | 8/1994 |
| JP | 7-41802 | 2/1995 |
| JP | 8-92605 | 4/1996 |
| JP | 8-182688 | 7/1996 |
| JP | 9-544 | 1/1997 |
| WO | WO 97/11038 | 3/1997 |

* cited by examiner

*Primary Examiner*—Ngoclan Mai
(74) *Attorney, Agent, or Firm*—Harness, Dickey & Pierce, P.L.C.

(57) ABSTRACT

To provide a method for forming undercuts of a metal injection molded product by simple processes and metal injection molded products having undercuts formed by the forming method thereof, steps are included of injection-molding a feed stock containing metal powder and binding resin, forming undercuts to an injection green body obtained by the injection-molding, and sintering after debinding the injection green body formed with undercuts. It is preferable that undercuts are formed by deforming at least one part of an injection green body; it is more preferable that they are deformed by pressing with a pressing member.

20 Claims, 8 Drawing Sheets

Debinding

METHOD OF FORMING UNDERCUT IN METAL POWDER INJECTION-MOLDED ARTICLE

TECHNICAL FIELD

The present invention relates to a method for forming undercuts of a metal injection molded product and metal injection molded products with undercuts.

TECHNICAL BACKGROUND

In orthodontics, an orthodontic apparatus such as brackets are directly bonded to the teeth normally by the use of adhesive or the like. Force is applied to the brackets by an orthodontic archwire, and the teeth are forcefully aligned in an appropriate position thereby.

Therefore, various proposals have been made so as to provide sufficient bonding strength to firmly hold an orthodontic apparatus in orthodontic treatment.

As one proposal thereof, undercuts, for instance, are provided on the bonding surface of an orthodontic apparatus to teeth. By providing undercuts, the area of the bonding surface increases, and the bonding strength increases, since there is an improvement in the holding power of the dental adhesive.

Methods of providing undercuts to a bonding surface described above include a method of forming undercuts by machining or the like as secondary work after manufacturing an orthodontic apparatus body, a method of fixing wire mesh to an orthodontic apparatus body by welding or the like, and so on.

However, according to the method of carrying out the above-noted secondary work, as an orthodontic apparatus is generally relatively small, there are problems such as extremely complex working, inferior productivity and high cost.

Moreover, a strong metal such as titanium is used for orthodontic apparatuses, so that the workability is poor and undercuts are extremely hard to form. Also, in the method of bonding the wire mesh by welding or the like, there is the problem that the mesh portion is buried by brazing filler metal during welding, and the bonding force between the wire mesh and the body gradually decreases.

On the other hand, orthodontic apparatus bodies have been recently manufactured by metal injection molding that have high yield, are flexible in molding shapes and can easily mold even complex shapes. Such an metal injection molding method is used for producing a metal body by debinding and sintering after injection-molding a feed stock mainly of metal powder and binding resin.

With such a metal injection molding method, one-body molding even into a complex shape is possible, but since a mold is used for injection-molding, undercuts cannot be directly molded without carrying out the secondary work to the sintered body.

The objective of the present invention is to provide a method for forming undercuts of a metal injection molded product by means of a simple process without the need for secondary work, and to provide metal injection molded products having undercuts.

DISCLOSURE OF THE INVENTION (1) A method for forming undercuts of a metal injection molded product according to the first invention comprises the steps of:

injection-molding a feed stock containing metal powder and binding resin;

forming undercuts to an injection green body provided by the injection molding; and sintering the injection green body having undercuts after debinding.

(2) It is preferable that the undercuts are formed by deforming at least one part of the injection green body.

(3) It is preferable that the undercuts be formed by heating and softening the injection green body.

(4) It is preferable that the undercuts be formed by pressing at least one part of the injection green body with a pressing member.

(5) It is preferable that the pressing surface of the pressing member be heated.

(6) It is preferable that the temperature of the pressing surface be 90° C. to 150° C.

(7) It is preferable that protrusions be formed on the pressing surface of the pressing member.

(8) It is preferable that pressing be carried out a plurality of times.

(9) It is preferable that pressing be carried out while changing the shape of the pressing surface.

(10) A method for forming undercuts of a metal injection molded product according to a second invention comprises the steps of:

injection-molding a feed stock containing metal powder and binding resin;

debinding an injection green body-molded by the injection-molding; and sintering a brown body provided by the debinding; wherein the injection green body is integrated with an undercut molding member in one body.

(11) It is preferable that the undercut molding member comprise a removable material by heating.

(12) It is preferable that the undercut molding member comprise a removable material in the debinding step.

(13) It is preferable that the undercut molding member comprise a material having resin as a main component.

(14) It is preferable that the resin have a melting point of 150° C. to 400° C.

(15) A method for forming undercuts of a metal injection molded product according to a third invention comprises the steps of:

injection-molding a feed stock containing metal powder and binding resin; and sintering an injection green body molded by the injection-molding after debinding;

wherein a mold for injection-molding which has a core for forming undercuts in the mold is used in the injection-molding step.

(16) It is preferable that the core is made up of an elastic material.

(17) It is preferable that the elastic material have a Vickers hardness of 40 to 100.

(18) It is preferable that the elastic material has tensile strength of 60 Kg/cm$^2$ or above.

(19) It is preferable that the elastic material consists of silicone rubber.

(20) It is preferable that a metal injection molded product of the preset invention be manufactured by the methods described in the above-noted items (1) or (19).

(21) It is preferable that the metal injection molded product be an orthodontic apparatus.

(22) It is preferable that the undercuts be provided to the tooth-bonding surface of the orthodontic apparatus.

Figure 1:
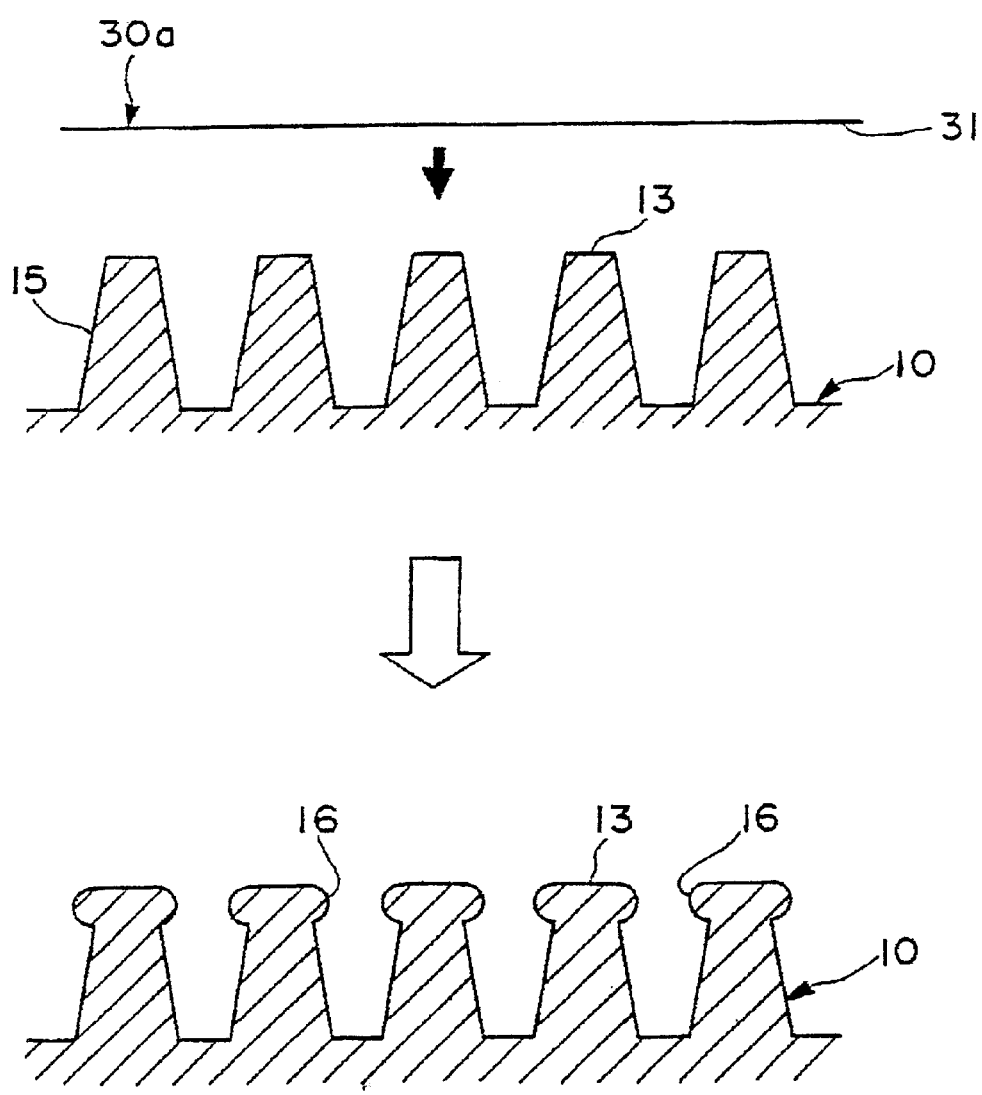
FIG. 1 is a partial sectional view showing a first embodiment of a method for forming undercuts of a metal injection molded product of the present invention.

EXPLANATION OF REFERENCE NUMERALS 1 orthodontic bracket
2 base
3 engagement part
4 bonding surface
7 slot
8 wire
9 tooth
10 injection green body
11 injection green body
13 protruding part
14 recessed part
15 tapered portion
16 undercut
30a, 30b, 30c pressing member
31 pressing surface
33, 35 protrusion
40 undercut molding member
41 green body
42 brown body
50 core
52 fin

BEST MODES FOR CARRYING OUT THE INVENTION

Methods for forming undercuts of a metal injection molded product of the present invention are explained in detail hereafter with reference to the preferred embodiments shown in the attached figures. A method for manufacturing an orthodontic apparatus (brackets) shown in FIG. 7, as a metal injection molded product with undercuts of the present invention, will be explained as an example.

Figure 2:
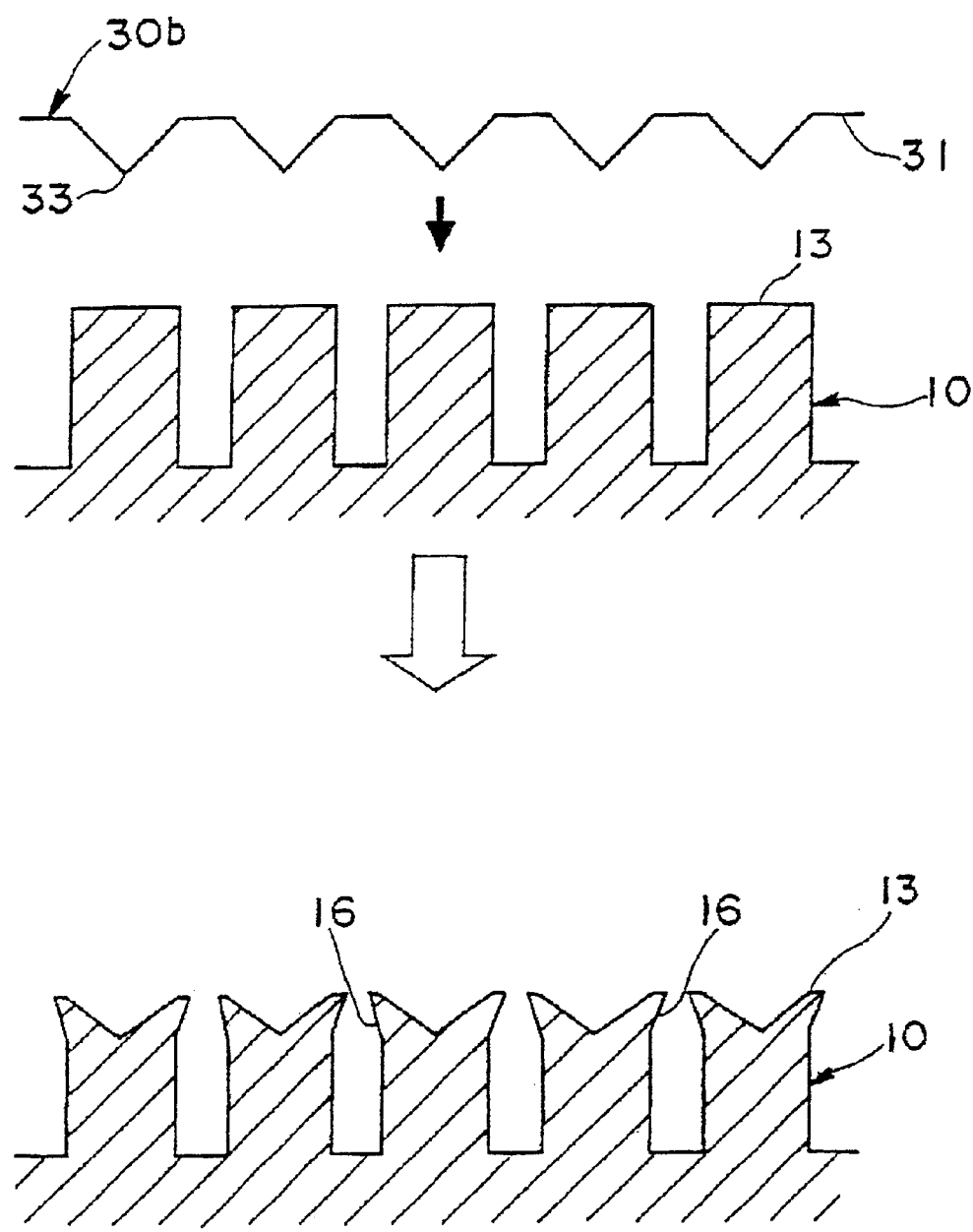
FIG. 2 is a partial sectional view showing the first embodiment of a method for forming undercuts of a metal injection molded product of the present invention.
Figure 3:
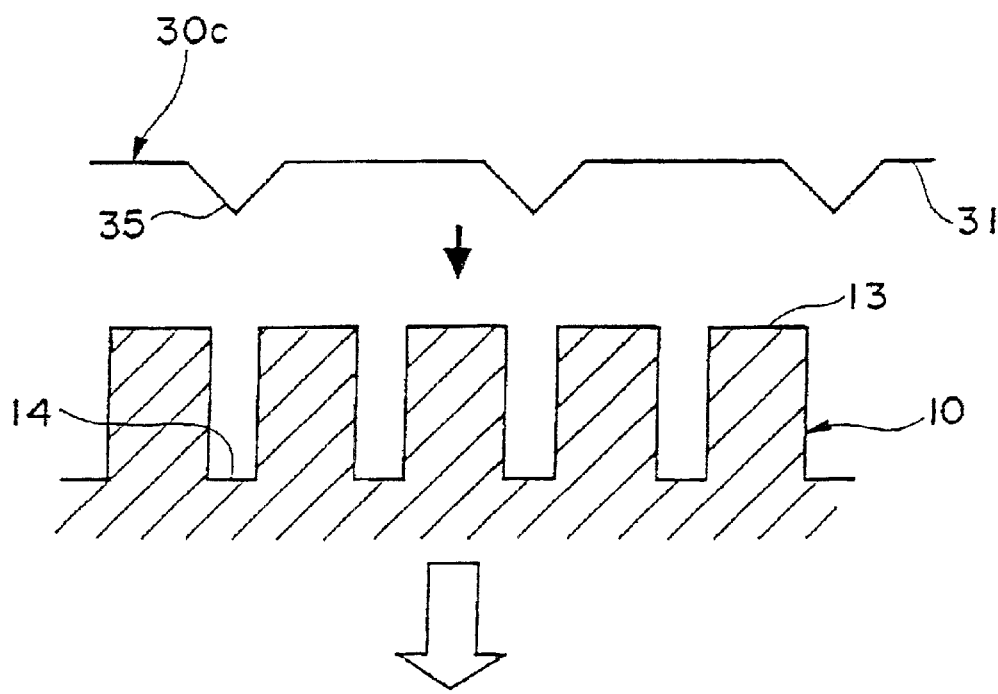
FIG. 3 is a partial sectional view showing the first embodiment of a method for forming undercuts of the metal injection molded product of the present invention.
Figure 3:
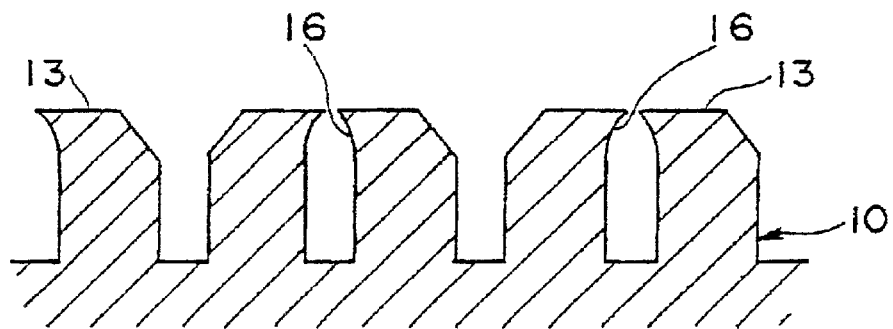

FIG. 1, FIG. 2 and FIG. 3 are partial sectional views showing a first embodiment of a method for forming undercuts of the metal injection molded product of the present invention.

A method for forming undercuts of a metal injection molded product of the present invention comprises the steps of injection-molding a feed stock containing metal powder and binding resin, forming undercuts to an injection green body obtained by the injection-molding, and sintering the injection green body with undercuts after debinding More specifically, a metal injection molded product may be manufactured by the steps described below.

First, a feed stock is prepared by mixing metal powder and binding resin by means of a kneading machine. Kneading may be carried out by the use of a kneading machine such as a kneader or a heating blender and the like.

Kneading conditions are appropriately selected based on various conditions such as particle diameter and the shape of metal powder, the type of binding resin, the amount of mixed additives and the like. If necessary, the feed stock may be pelletized.

It is preferable that the ratio of metal powder in the feed stock be in the range of 80 wt. % to 98 wt. %. By setting the ratio of metal powder in this range, the feed stock has moderate flowability, excellent molding properties, and can provide a preferable sintered portion.

There is no particular limitation to the metal powder; however, in manufacturing an orthodontic apparatus or the like, it is preferable to use a dental metallic material such as titanium, titanium alloy and stainless steel. Titanium and titanium alloy are particularly preferable thereof.

Since an orthodontic apparatus is forcefully pulled by a metal wire or the like, it must have a high level of strength and toughness so as not to be damaged during its use. By using titanium or titanium alloy, these conditions can be easily satisfied. Furthermore, titanium or titanium alloy is extremely high in affinity for the human body and is particularly suitable as a material for an orthodontic apparatus.

Binding resin includes, for instance, polypropylene resin, polyethylene resin, acrylic resin, polystyrene resin, various kinds of waxes, and so on, and one kind or at least two kinds thereof may be mixed and kneaded for use. Moreover, in addition to the above-described metal powder and binding resin, various kinds of additives such as plasticizers, lubricants, antioxidants, debinding accelerators and surface active agents may be added, depending upon the need.

The feed stock prepared thereby is injection-molded by an injection-molding machine. Molding conditions of injection-molding are not particularly limited, and are appropriately set in accordance with the composition, viscosity, and the like of the feed stock. However, it is preferable that material temperature be about 20° C. to 200° C. and that the injection pressure be about 30 kgf/cm$^2$ to 150 kgf/cm$^2$.

As a mold for injection-molding, the same mold as a mold for plastic molding may be generally used; however, in manufacturing a fine and complex green body as, for instance, an orthodontic apparatus, it is preferable to use a hot runner or the like.

FIG. 1 is a cross-sectional view showing one part of an injection green body extracted from a mold for injection-molding.

A plurality of protruding parts 13 are formed in an injection green body 10. It is preferable that about sixteen to one thousand six hundred protruding parts 13 be arranged per 1 cm$^2$. The protruding part 13 has a tapered portion 15 with a decreasing width along the extraction direction of the mold.

As these protruding parts 13 of the injection green body 10 are pressed by a pressing member 30a, tips of the protruding parts 13 are deformed and undercuts 16 are formed. Thus, if an injection green body is not yet sintered, it would be possible to deform at least one part thereof and to easily form the desirable. undercuts.

Forming undercuts by deforming the injection green body 10 are preferably done by heating and softening. The unsintered injection green body 10 contains binding resin and has thermoplasticity, so that it can be easily deformed by heating.

Methods of heating, softening and then deforming the injection green body 10 are not particularly limited, and include a method of contacting the body with a hot member, a method of adding high energy such as irradiation of high-frequency, a laser beam or the like without contacting, and so on.

In case of this embodiment, the pressing surface 31 of the pressing member 30a is heated, and the tips of the protruding parts 13 are heated and softened by contacting them with this pressing surface 31, thus forming undercuts 16 by pressing further.

The temperature of the pressing surface 31 may be optionally selected, but is preferably 90° C. to 150° C. If the temperature of the pressing surface 31 is too high, the injection green body 10 would be softened sharply and maintaining the shape would sometimes be difficult. Moreover, decomposition, gasification and the like of the binding resin are likely to occur. On the other hand, when the heating temperature is too low, the injection green body 10 is sometimes not softened at all, and when pressed in such a condition, a part or a whole body of the injection green body 10 is broken, cracked and so forth, thus often damaging the shape.

FIG. 2 is a cross-sectional view showing another example of molding undercuts in this embodiment.

As with the above-described case, the injection green body 10 is formed with a plurality of protruding parts 13. These protruding parts 13 may or may not be tapered; however, in this embodiment, they are not tapered.

Protrusions 33 are formed on the pressing surface 31 of a pressing member 30b so as to match the protruding parts 13.

The protrusions 33 and the protruding parts 13 mutually face each other, and as they are mutually pressed, the protrusions 33 are imbedded in the protruding parts 13 and tips of the protruding parts 13 are then deformed and split. These split pieces are pushed outward relative to the pressing direction, thus forming undercuts 16.

Moreover, the shape, arrangement and so forth of the protrusions 33 formed at the pressing surface 31 may be optionally selected and set. Furthermore, as the protruding parts that are formed on the pressing surface 31, pins or the like may be imbedded.

As in this embodiment, the locations, arrangement and so forth of the undercuts may be arranged by forming the protrusions on the pressing surface of the pressing member. Therefore, depending upon the purpose, and objective and so forth of the injection molded product, desirable undercuts may be formed.

It is preferable that the pressing surface 31 be heated at 90° C. to 150° C. as in the above-mentioned case.

FIG. 3 is a cross-sectional view showing another example of the molded undercuts in this embodiment.

The same ones as in FIG. 2 may be used for the injection green body 10 and the pressing member 30c.

As shown in the figure, protrusions 35 are formed on the pressing surface 31 of the pressing member 30c so as to face each recessed part 14.

As the tips of the protrusions 35 are pressed so as to face the recessed parts 14, the protrusions 35 are pressed into the recessed parts 14. As a result, the tips of the protruding parts 13 adjoining recessed parts 14 are pushed aside, thereby forming undercuts 16.

It is preferable that the pressing surface 31 be heated at 90° C. to 150° C. as in the above-mentioned case.

Moreover, the shape, arrangement and so forth of the protrusions 35 formed on the pressing surface 31 may be optionally selected and set. Furthermore, as the protrusions that are formed at the pressing surface 31, pins or the like may be imbedded.

Additionally, in case of forming undercuts with a pressing member, pressing may be done once or more.

In pressing several times, pressing may be repeated with the pressing surface having an identical shape or with a pressing surface of a different shape; however, it is preferable to press using pressing surfaces of different shapes. By the combination of pressing surfaces of different shapes, various undercuts may be formed.

Then, the injection green body 10 formed with undercuts thereby is debinded.

Debinding is carried out by means of heat treatment in a non-oxidizing atmosphere, for instance, under a vacuum or in a low-pressure condition (e.g., $1 \times 10^{-1}$ Torr to $1 \times 10^{-6}$ Torr) or in an inert gas such as nitrogen gas and argon gas, and by the evaporation or decomposition of the binding resin. Debinding conditions such as temperature increase rate, debinding temperature, and so forth may be set so as not to evaporate or decompose the binding resin rapidly, and to avoid reactions between the binding resin and the metal powder. It is preferable that the debinding temperature be in the range of, for instance, 150° C. to 750° C.

Finally, a brown body is sintered.

It is preferable that sintering be carried out at a low-pressure of $1 \times 10^{-2}$ Torr or below (more preferably, $1 \times 10^{-2}$ Torr to $1 \times 10^{-6}$ Torr) or in a vacuum, or in an inert gas atmosphere such as nitrogen gas and argon gas at 1 Torr to 760 Torr.

The sintering temperature and sintering time are set so as to diffuse and grow metal powder grains to be crystal grains by sintering, so that the powder will be a dense sintered body as a whole, in other words, a body with high density and low porosity.

It is preferable that the sintering temperature be 1000° C. to 1500° C., and that the sintering time be 0.5 hours to 10 hours.

After sintering, a metal injection molded product with undercuts is provided.

According to the method of the present invention, metal injection molded products having undercuts may be easily obtained without secondary working and with only continuous processes.

Moreover, without requiring a particular injection mechanism or a mold structure, pressing members (pressing surfaces) are exchanged, so that it is possible to mold undercuts in a preferable size, shape and arrangement depending upon the purpose.

Figure 4:
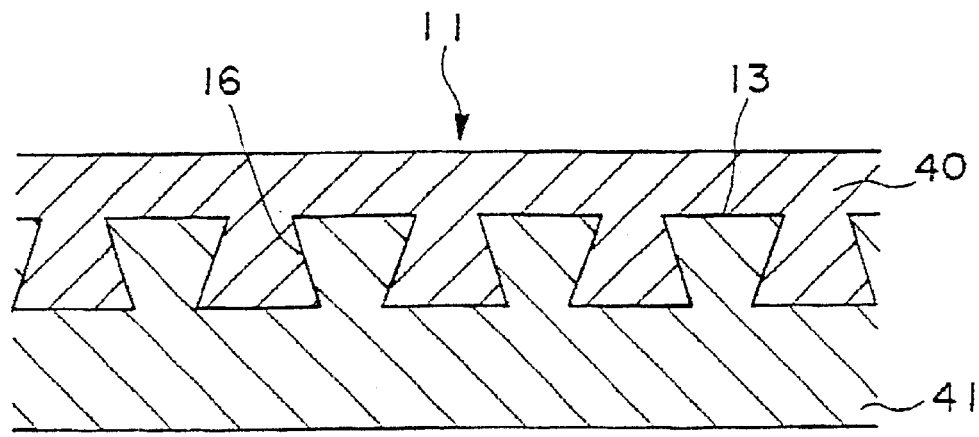
FIG. 4 is a partial sectional view showing a second embodiment of a method for forming undercuts of the metal injection molded product of the present invention.
Figure 4:
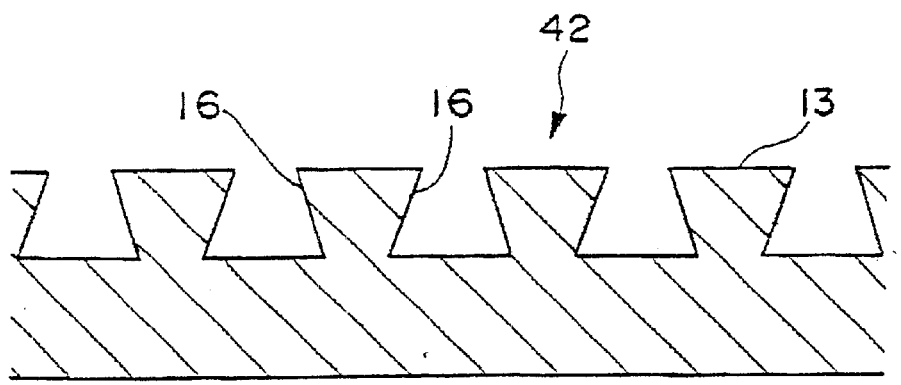

FIG. 4 is a partial sectional view showing a second embodiment of a method for forming undercuts of a metal injection molded product of the present invention.

The present invention is a method for forming undercuts of a metal injection molded product comprising the steps of injection-molding a feed stock containing metal powder and binding resin, debinding an injection green body molded by means of the injection molding, and sintering a brown body obtained by debinding; wherein the injection green body is integrated with an undercut molding member in one body.

Feed stock preparation and injection-molding conditions, and the like are the same as in the first embodiment. Mostly, the differences from the first embodiment are explained hereafter, and items having the same explanation will be omitted.

FIG. 4 is a partial sectional view showing a part of an injection green body and a brown body in this embodiment.

As shown in this figure, the injection green body 11 is made up of a green body 41 consisting of a feed stock which contains metal powder and binding resin, and an undercut molding member 40. The green body 41 and the undercut molding member 40 are mutually joined together into one body on the protruding parts 13 of the green body 41.

Such an injection green body 11 may be obtained by injection-molding a feed stock while first filling the undercut molding member 40 into a mold for injection-molding as a core.

For materials of the undercut molding member 40, any material is acceptable as long as it is removable and does not damage the shape of the green body 41 or the brown body 42, including e.g. any decomposable and removable material by heating, dissolving or other methods. Among these, a removable material by heating is preferable, and a removable material in the debinding step is further preferable. Debinding the green body 41 and removing the undercut molding member 40 may be carried out simultaneously in one step.

As such a material for the undercut molding member 40, there are no particular limitations as long as the material can hold a shape even with the injection temperature of a feed stock during injection-molding, and is removable along with binding resin in the debinding step. A material containing resin as a main component is preferable, and a resin material having a melting point of 150° C. to 400° C. is more preferable. Such resins include e.g. polypropylene, polyethylene, polystyrene, polyacetal, acrylic resin, and so forth.

The undercut molding member 40 is removed from the injection green body 11 thereby, thus providing the brown body 42 that is molded with the undercuts 16 as shown in the figure.

By sintering the brown body 42 as in the first embodiment, a metal injection molded product having undercuts may be provided. The undercut molding member 40 is used as in this embodiment that consists of a removable material by heating or the like after injection-molding. Thus, there will be no limitations on mold-release from a mold for injection-molding, flexibility on the shapes and sizes of a green body will improve sharply; and any undercuts may be formed.

Figure 5:
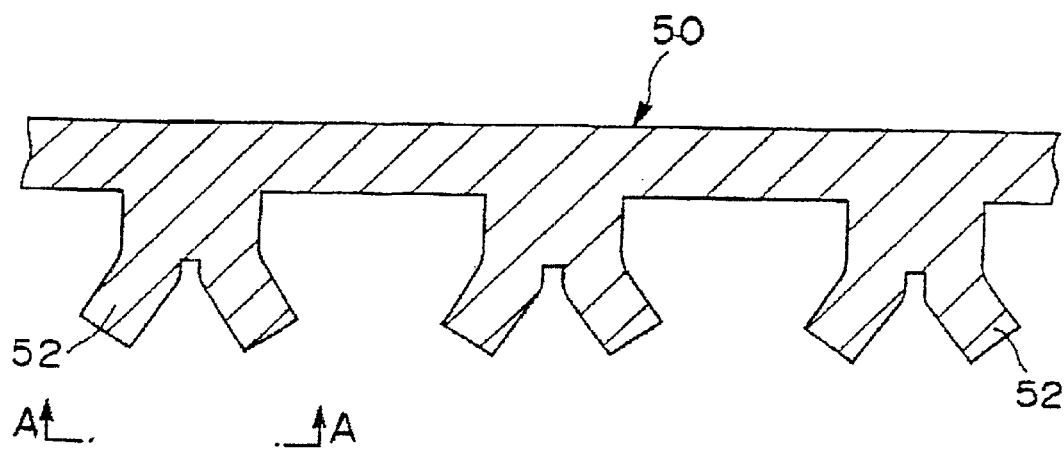
FIG. 5 is a partial sectional view showing a third embodiment of a method for forming undercuts of the metal injection molded product of the present invention.
Figure 6:
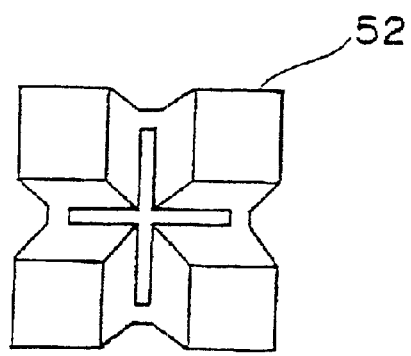
FIG. 6 is a view taken on line A—A of FIG. 5.

FIG. 5 and FIG. 6 are partial sectional views showing a third embodiment of the method for forming undercuts of a metal injection molded product of the present invention.

The present invention is a method for forming undercuts of a metal injection molded product comprising the steps of injection-molding a feed stock containing metal powder and binding resin, and sintering an injection green body molded by injection-molding after debinding; whereas a mold for injection-molding having a core for forming undercuts in the mold is used in the injection-molding step.

The same feed stock preparation, injection-molding conditions, and so forth may be carried out as in the first embodiment and the second embodiment mentioned above.

Mostly, differences between the first embodiment and the second embodiment will be explained, and explanations which are the same will be omitted. FIG. 5 is a partial sectional view showing one example of a core provided in a mold for injection-molding used in this embodiment. FIG. 6 is a view taken on line A—A of FIG. 5.

The core 50 is formed with a fin 52 as shown in the figure. The fin 52 has its tips split four ways, and an injection green body is formed with undercuts by the shape of this fin 52.

It is preferable that such a core 50 be made up of an elastic material. The fin 52 can be stretched or deformed, and may be easily released from the undercuts 16 of the injection green body 10.

The fin 52 has open tips as shown in FIG. 5 and FIG. 6. When the fin 52 maintains this shape after injection-molding, it engages in the releasee direction of the core 50, so that release from the injection green body 10 will be extremely difficult. However, when the fin 52 has elasticity as in the present invention, the tips of the fin 52 close as the core 50 is being released, so that releasing becomes possible.

By fully utilizing characteristics such as flexibility and deformation of an elastic material as described above, it is possible to easily remove, from a mold, an injection green body with undercuts which could not be removed solely by opening and closing the mold. As the elastic material constituting the core 50, material having a Vickers hardness of 40 to 100 is, for instance, preferable. With below 40 in hardness, sufficient rigidity and shape maintaining properties cannot be obtained as a core; and at above 100, the fin 52 cannot be fully deformed, causing problems such as scratching the injection green body 10 during extraction.

Moreover, the tensile strength is preferably 60 Kg/cm$^2$ or above.

At less than 60 Kg/cm$^2$ of tensile strength, the strength will not be sufficient to withstand stress during extraction, and extraction will be sometimes difficult.

Materials of such a core 50 include EVA resin (ethylene-vinyl acetate copolymer), chlorinated polyethylene, thermoplastic elastomer, rubber material (natural rubber, synthetic rubber), and the like. Examples of synthetic rubber include e.g. polyisoprene rubber, butadiene rubber, 1,2-polybutadiene rubber, styrene-butadiene rubber, chloroprene rubber, nitrile rubber, butyl rubber, ethylene-propylene rubber, chlorosulfonated polyethylene, acrylic rubber, epichlorohydrine rubber, silicone rubber, fluoro-rubber, urethane rubber, and the like. These rubber materials may be used solely or as a mixture of two or more kinds; however, among these, silicone rubber is preferable. Silicone rubber is applicable in a wide temperature range and is excellent in heat resistance, oil resistance and weather resistance. Thus, it is not transformed, decomposed, etc. by temperature and pressure during injection-molding, and the shape of the fin 52 may be kept well. Moreover, it is unlikely that the rubber will react to feed stock components such as metal powder.

The core 50 may be entirely made up of an elastic material like silicone rubber in the present invention, or may be made up of an elastic material, a metal material, and so forth. In this case, it is preferable that at least fin 52 be made up of an elastic material such as silicone rubber and that other parts be made up of a metal material or the like.

After the core 50 is removed, a metal injection molded product having undercuts may be obtained by debinding and sintering the injection green body 10 as in the first embodiment.

The undercuts formed as in the above-mentioned embodiment may have a constant or irregular pattern. Also, undercuts may be formed so as to keep the angles and sizes thereof the same, or to change angles and so forth irregularly based on a predetermined order.

Moreover, a metal injection molded product with undercuts that is molded in the present invention may be for any use, but includes, for example, an orthodontic apparatus.

Figure 7:
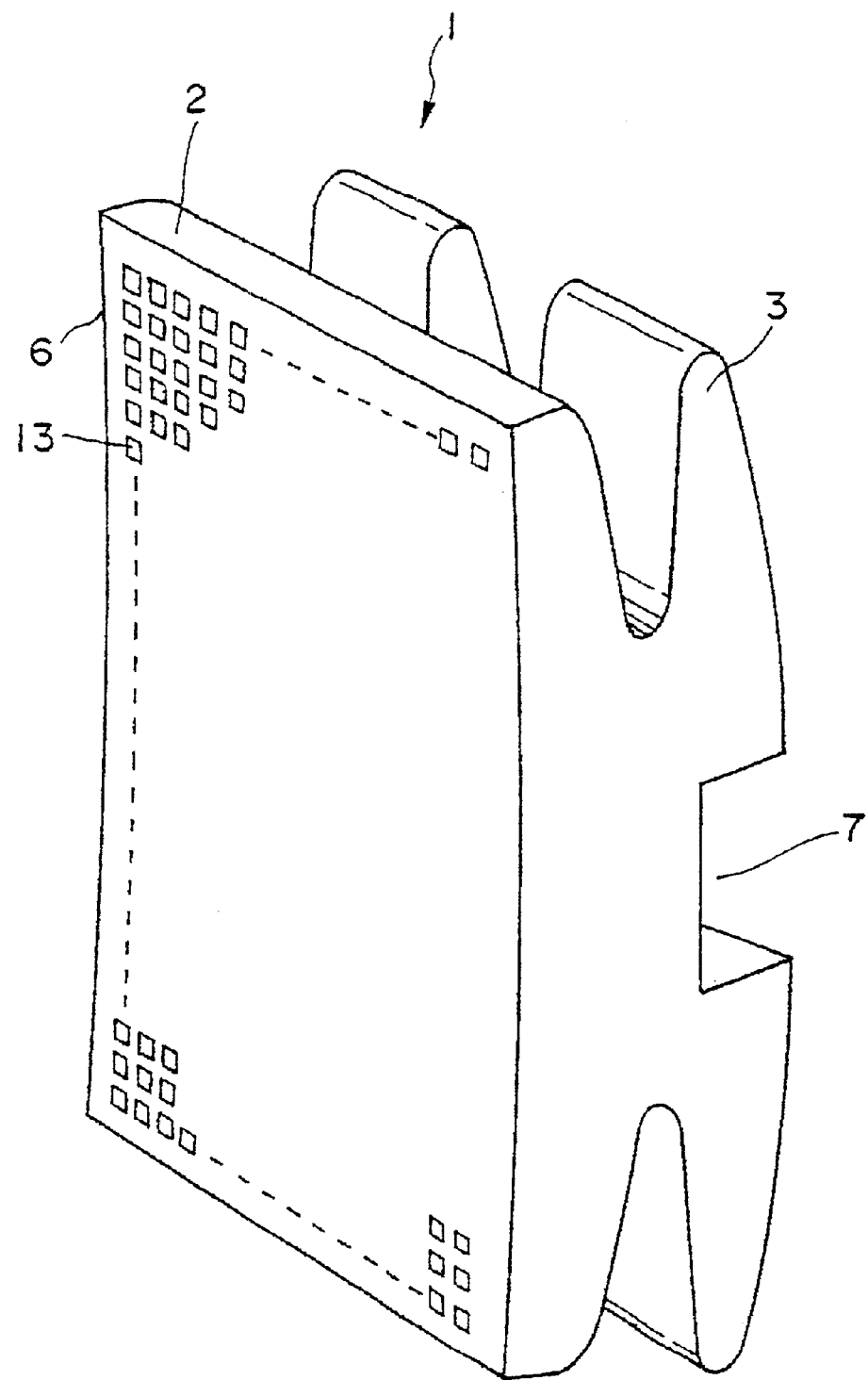
FIG. 7 is a stereoscopic perspective view of an orthodontic apparatus prepared by the present invention.
Figure 8:
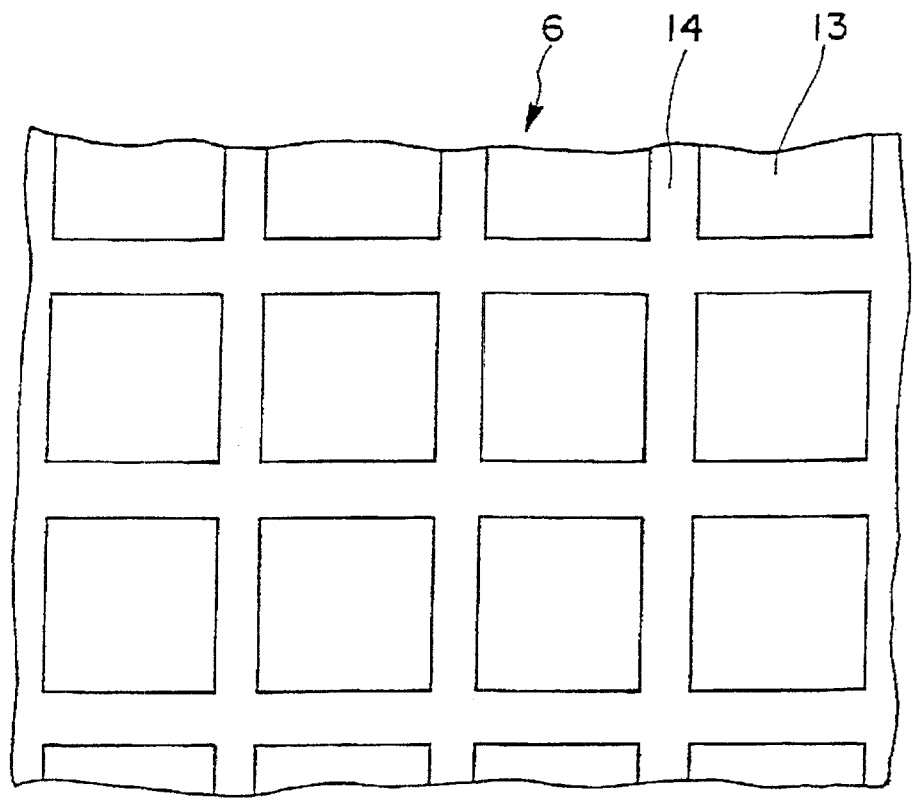
FIG. 8 is an enlarged view of the orthodontic apparatus shown in FIG. 7.
Figure 9:
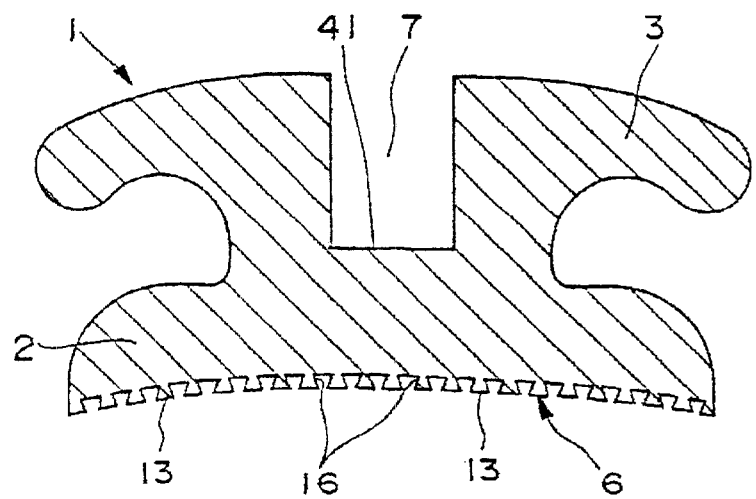
FIG. 9 is a cross-sectional view of the orthodontic apparatus shown in FIG. 7.

In the case of an orthodontic apparatus, as shown in FIG. 7 and FIG. 9, it is preferable to form undercuts 16 to a bonding surface 6 to teeth. As a result, a surface area of the bonding surface 6 will increase, and adhesion will be fully maintained, providing excellent adhesive strength.

Methods for forming undercuts of metal injection molded products having undercuts of the present invention were explained above by referring to each embodiment shown in figures, but the present invention is not limited to these. For instance, as an undercut molding member, resinous beads or the like may be used.

Embodiments

Next, specific embodiments of the present invention will be explained.

Embodiment 1

Titanium powder (average particle size: 15 μm, 92 wt. %), polypropylene as binding resin, ethylene-vinyl acetate copolymer(EVA), and other various additives (paraffin wax, dibutylphthalate) were mixed at a predetermined ratio, and were kneaded by a kneading machine, thus preparing a feed stock.

Then, this feed stock was heated to melt the binding resin and was injected into a mold for injection-molding, thus providing an injection green body 10.

The tips of protruding portions 13 of this injection green body 10 were pressed with a pressing member 30*a* having a pressing surface 31 with the shape shown in FIG. 1 and heated at 120° C., thus forming undercuts 16.

The injection green body 10 formed with undercuts 16 was heated for one hour at 450° C. in vacuum by a predetermined debinding furnace, decomposing and removing the binding resin and the additives without damaging the shape of the green body and thus providing a brown body.

Then, the brown body was shifted to a sintering furnace, and was sintered for three hours at 1,200° C. in argon gas and was then cooled, providing an orthodontic bracket 1 formed with undercuts 16 at the bonding surface 6 as shown in FIG. 7 or FIG. 9.

Each part of this orthodontic bracket 1 has the following shape:

Size of base 2: 5 mm×5 mm

Protruding parts 13: 100 per 1 cm$^2$

Depth of recessed part of an undercut 16: 0.3 mm

Depth of a slot 7: 2.5 mm, Width thereof: 1.3 mm

Embodiment 2

A feed stock having the same composition as in Embodiment 1 was prepared.

Then, an undercut molding member 40 as shown in the figure (made of polystyrene; melting point of 200° C.) was provided inside a mold for injection-molding. A feed stock was injected into this mold for injection-molding as in Embodiment 1, thus providing an injection green body 11 as shown in FIG. 4.

This injection green body 11 was heated for 1.5 hours in nitrogen gas by a predetermined debinding furnace; the binding resin and the additives were decomposed and removed; and at the same time, the undercut molding member 40 was removed, thus providing a brown body 42 formed with undercuts 16.

Then, this brown body 42 was shifted to a sintering furnace, and was sintered for three. hours at 1,200° C. in vacuum and was then cooled, providing the orthodontic bracket 1 as in Embodiment 1.

Embodiment 3

A feed stock having the same composition as in Embodiment 1 was prepared.

Then, this feed stock was heated to melt the binding resin, and was injected into a mold for injection-molding. In the mold for injection-molding, a core 50 made of silicone resin having a shape as shown in FIG. 5 was provided in advance.

After the injected feed stock was solidified, the mold for injection-molding was opened and the core 50 was pulled out from the injection green body. The tips of the fin 52 were closed as the core 50 was pulled out of the injection green body, so that it was possible to extract the core without damaging the undercut shape of the injection green body.

The injection green body formed with the undercuts thereby was debinded and sintered as in Embodiment 1, thus providing the same orthodontic bracket 1 as in Embodiment 1.

Figure 10:
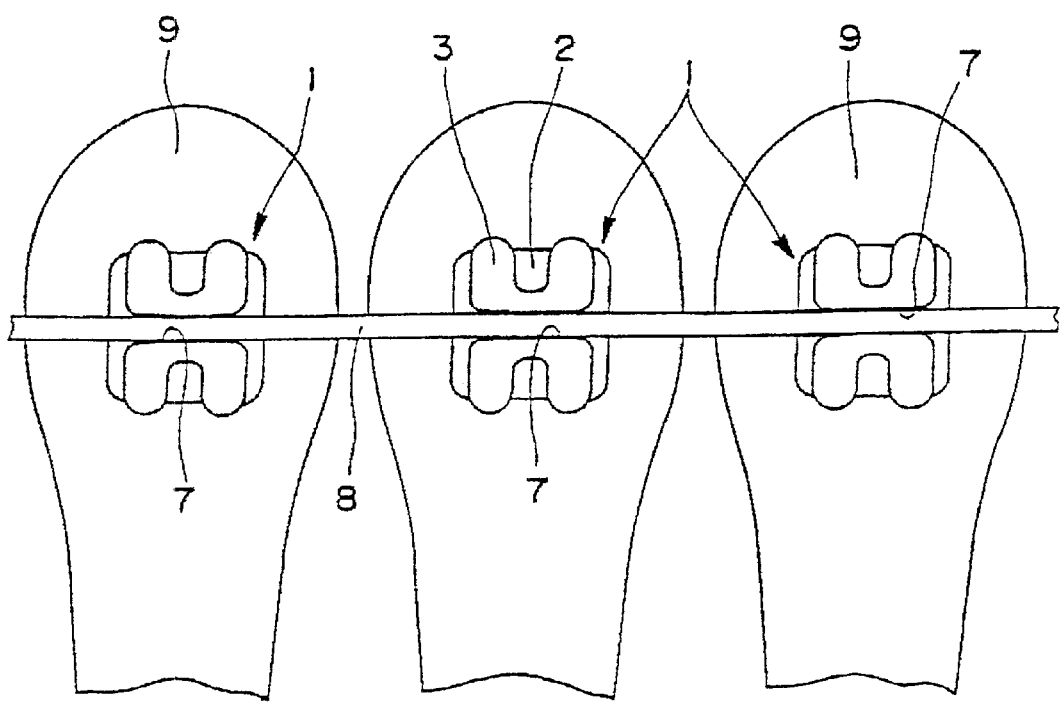
FIG. 10 is a plane view showing the use of an orthodontic apparatus prepared by the present invention.

Dental adhesive was coated onto the bonding surface 6 of each orthodontic bracket 1 prepared in Embodiments 1 to 3, and was fixed to the surface of a tooth 9 as shown in FIG. 10. Then, a stainless wire 8 was passed through slots 7 provided at engagement parts 3 of brackets 1, and was mounted.

One end of the wire 8 was fixed in this condition and sufficient tension was added by pulling the other end. The brackets 1 were preferably fixed to the teeth 9, and there appeared to be no shaky, separated or so forth brackets 1.

As described above, according to the method of the present invention, a metal injection molded product having undercuts can be provided without requiring unique mold structures or the like, and without requiring complex secondary processing. Furthermore, undercut patterns and the like may be easily arranged and changed.

When a metal injection molded product with undercuts is an orthodontic apparatus, a bonding area increases due to the formation of undercuts and bonding strength to teeth may be maintained and improved. Furthermore, by selection of angles, locations and the like of undercuts, bonding strength may be preferably arranged.

INDUSTRIAL APPLICATIONS

Metal injection molded products of the present invention are suitable for, for instance, an orthodontic apparatus.

What is claimed is:

1. A method for forming undercuts of a metal injection molded product comprising the steps of:

injection-molding a feed stock containing metal powder and binding resin;

forming undercuts to an injection green body provided by the injection molding wherein the undercuts are formed by pressing at least one part of the injection green body with a pressing member having a heated pressing surface; and sintering the injection green body formed with undercuts after debinding.

2. The method of claim 1, wherein the undercuts are formed by heating and softening the injection green body.

3. The method of claim 1, wherein temperature of the pressing surface is 90° C. to 150° C.

4. A method for forming undercuts of a metal injection molded product comprising the steps of:

injection-molding a feed stock containing metal powder and binding resin;

forming undercuts to an injection green body provided by the injection molding, wherein the undercuts are formed by pressing at least one part of the injection green body with a pressing member, wherein protrusions are formed at a pressing surface of the pressing member.

5. The method of claim 1, wherein the pressing is carried out a plurality of times.

6. The method of claim 5, wherein the pressing is carried out while changing a shape of the pressing surface.

7. A method for forming undercuts of a metal injection molded product comprising the steps of:

injection-molding a feed stock containing metal powder and binding resin; and sintering an injection green body molded by the injection-molding after debinding;

wherein a mold for injection molding having a core made up of an elastic material for forming undercuts in the mold is used in the injection-molding step.

8. The method of claim 7, wherein the elastic material has a Vickers hardness of 40 to 100.

9. The method of claim 7, wherein the elastic material has tensile strength of 60 kg/cm$^2$ or above.

10. The method of claim 7, wherein the elastic material consists of silicone rubber.

11. The method of claim 4, wherein the undercuts are formed by heating the pressing member and softening the injection green body with the pressing member.

12. The method of claim 4, wherein the pressing is carried out a plurality of times.

13. The method of claim 12, wherein the pressing is carried out while changing a shape of the pressing surface.

14. A method for forming undercuts of a metal injection molded product comprising the steps of:

injection-molding a feed stock containing metal powder and binding resin;

forming undercuts to an injection green body provided by the injection molding, wherein the undercuts are formed by heating and softening the injection green body; and sintering the injection green body formed with undercuts after debinding.

15. The method of claim 14, wherein said step of heating and softening the injection green body further comprises pressing at least one part of the injection green body with a pressing member.

16. The method of claim 15, wherein a pressing surface of the pressing member is heated.

17. The method of claim 16, wherein temperature of the pressing surface is 90° C. to 150° C.

18. The method of claim 15, wherein protrusions are formed at a pressing surface of the pressing member.

19. The method of claim 18, wherein the pressing is carried out a plurality of times.

20. The method of claim 19, wherein the pressing is carried out while changing a shape of the pressing surface.

* * * * *

UNITED STATES PATENT AND TRADEMARK OFFICE
CERTIFICATE OF CORRECTION

PATENT NO.    : 6,444,167 B1
DATED         : September 3, 2002
INVENTOR(S)   : Shimodaira et al.

It is certified that error appears in the above-identified patent and that said Letters Patent is hereby corrected as shown below:

Column 1,
Line 49, "an" should be -- a --

Column 3,
Line 1, "Drawing" should be -- Drawings --

Column 8,
Line 16, "releasee" should be -- release --

Column 10,
Line 59, after "body" insert -- by using the pressing member having the heated pressing surface --

Signed and Sealed this

Fourth Day of February, 2003

JAMES E. ROGAN
*Director of the United States Patent and Trademark Office*